(12) United States Patent
Huang et al.

(10) Patent No.: US 7,201,928 B1
(45) Date of Patent: Apr. 10, 2007

(54) EXTRACTS OF ORANGE PEEL FOR PREVENTION AND TREATMENT OF CANCER

(75) Inventors: Mou Tuan Huang, Englewood Cliffs, NJ (US); Chi-Tang Ho, East Brunswick, NJ (US); Robert T. Rosen, Monroe Township, NJ (US); Geetha Ghai, Murray Hill, NJ (US); Martin Lipkin, New York, NY (US); Kuang Yu Chen, Belle Mead, NJ (US); Nitin Telang, Pelham Manor, NY (US); Charles Boyd, Honolulu, HI (US); Katalin Csiszar, Honolulu, HI (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 10/088,664

(22) PCT Filed: Sep. 20, 2000

(86) PCT No.: PCT/US00/25733

§ 371 (c)(1),
(2), (4) Date: Aug. 15, 2002

(87) PCT Pub. No.: WO01/21137

PCT Pub. Date: Mar. 29, 2001

Related U.S. Application Data

(60) Provisional application No. 60/155,018, filed on Sep. 21, 1999.

(51) Int. Cl.
 A61K 36/00 (2006.01)
 A61K 36/752 (2006.01)
 A61N 65/00 (2006.01)
(52) U.S. Cl. .................. 424/736; 424/725; 424/777
(58) Field of Classification Search ............ 424/430, 424/436, 439, 725, 729, 736, 746, 750, 777; 514/966, 967, 825, 826
See application file for complete search history.

(56) References Cited

U.S. PATENT DOCUMENTS

| | | | |
|---|---|---|---|
| 3,867,541 A | 2/1975 | Robbins | |
| 3,903,266 A | 9/1975 | Robbins | |
| 5,041,425 A | 8/1991 | Hasegawa et al. | |
| 5,580,545 A * | 12/1996 | Washino et al. | 424/49 |
| 5,830,738 A * | 11/1998 | Thomas et al. | 209/209 |
| 5,859,293 A * | 1/1999 | Bailey et al. | 562/467 |
| 6,184,246 B1 | 2/2001 | Manthey et al. | |
| 6,221,357 B1 | 4/2001 | Bok et al. | |
| 6,239,114 B1 | 5/2001 | Guthrie et al. | |
| 6,251,400 B1 | 6/2001 | Guthrie et al. | |
| 6,706,256 B2 * | 3/2004 | Lawlor | 424/58 |

FOREIGN PATENT DOCUMENTS

| | | |
|---|---|---|
| CN | 1030078 | 1/1989 |
| CN | 1049340 | 2/1991 |
| CN | 1069200 | 2/1993 |
| CN | 1094957 | 11/1994 |
| CN | 1100322 | 3/1995 |
| CN | 1105853 | 8/1995 |
| CN | 1108554 | 9/1995 |
| CN | 1139007 | 1/1997 |
| CN | 1145804 | 3/1997 |
| CN | 1170592 | 1/1998 |
| CN | 1191746 | 3/1998 |
| CN | 1279905 | 1/2001 |
| CN | 1301507 | 7/2001 |
| CN | 1071576 | 9/2001 |
| DE | 39 22 666 | 7/1989 |
| JP | 60-199817 | 10/1985 |
| JP | 9-295932 | 11/1997 |
| JP | 2000-83654 | 9/1998 |
| JP | 3010210 | 12/1999 |
| JP | 2000-80035 | 3/2000 |
| JP | 2000083654 * | 3/2000 |
| JP | 2004-137218 | 5/2004 |
| WO | WO 1999/15167 | 4/1999 |
| WO | WO 1999/52380 | 10/1999 |
| WO | WO 1999/62358 | 12/1999 |
| WO | WO 2000/07607 | 2/2000 |
| WO | WO 2000/32062 | 6/2000 |
| WO | WO 2000/64282 | 11/2000 |
| WO | WO 2000/76492 | 12/2000 |
| WO | WO 2001/51043 | 7/2001 |
| WO | WO 2001/70029 | 9/2001 |

OTHER PUBLICATIONS

Nagy et al. Citrus Science and Technology, 1977, AVI, Westport, vol. 1, pp. 416-417.*
Malterud et al. J. Agric. Food Chem., 2000, 48, pp. 5576-5580.*
Peirce, A. The American Pharmaceutical Association Practical Guide to Natural Medicines, 1999, Stonesong Press, Inc., pp. 563-566.*
Madis Botanicals, Inc., Resverapure™ Resveratrol PE 8%, Product Code 04544, p. 2, Lines 6-7 and 15-31, 1997.*
Castleman, M., The Healing Herbs, The Ultimate Guide to the Curative Power of Nature's Medicines, 1991, Rodale Press, Emmaus, PA. p. 349.*
Plant Specimen (http://www.cresentbloom.com/Specimen/C1 /default.htm.*

(Continued)

*Primary Examiner*—Christopher Tate
*Assistant Examiner*—Kailash C. Srivastava
(74) *Attorney, Agent, or Firm*—Jones Day

(57) ABSTRACT

Compositions and methods of inhibiting tumor cell growth and treating and preventing cancer are provided based on administration of an orange peel extract either alone or in combination with other phytochemicals.

12 Claims, No Drawings

OTHER PUBLICATIONS

Xu et al. 1993. Effects of fruit juicesyprocessed vegetable juice, orange peel and green tea on endogenous formation of N-nitrosoproline in subjects from a high-risk area for gastric cancer in Moping County,china. Eur J of Cancer Prevention, vol. 2: 327-33.*

Kuo S. M., (1997) "Dietary flavonoid and cancer prevention: evidence and potential mechanism", Critical Reviews™ in Oncogenesis, vol. 8, 1, pp. 47-49.

Lamartiniere et al., (1995). "Neonatal genistein chemoprevents mammary cancer", Proc. Soc. Exp. Biol. Med., vol. 208, pp. 120-123.

Mak et al., (1996). "Isolation of anti-leukemia compounds from citrus reticulata", Life Sciences, vol. 58, 15, pp. 1269-1276.

Miyazawa et al., (1999). "Antimutagenic activity of polymethoxyflavonoids from citrus aurantium". J. Agric. Food Chem.. vol. 47, pp. 5239-5244.

Murakami et al., (2000). "Suppressive effects of citrus fruits on free radical generation and nobiletin, an anti-inflammatory polymethoxyflavonoid". Biofactors. vol. 12, 1-4, p. 6.

Robbins R.C., (1988). "Flavones in citrus exhibit antiadhesive action on platelets", Florida Agricultural Experiment Station Journal, Series No. 9146, pp. 418-421.

Rogers et al., (1998), "Black tea and mammary gland carcinogenesis by 7,12-dimethylbenz[a]anthracene in rats fed control or high fat diets", Carcinogenesis, vol. 19, 7, pp. 1269-1273.

Singletary et al., (1996), "Inhibition by rosemary and carnosol of 7,12-dimethylbenz[a]anthracene (DMBA)-induced rat mammary tumorigenesis and in vivo DMBA-DNA adduct formation", Cancer Letters, vol. 104, pp. 43-48.

Singletary et al., (1991), "Inhibition of 7,12-dimethylbenz[a]anthracene (DMBA)-induced mammary tumorigenesis and of in vivo formation of mammary DMBA-DNA adducts by rosemary extract", Cancer Letters, vol. 60, pp. 169-175.

Stoner et al., (1995). "Polyphenols as cancer chemopreventive agents", Journal of Cellular Biochemistry, Supplement, vol. 22, pp. 169-180.

Takase et al., (1994), "Pharmacological profile of gastric mucosal protiection by marmin and nobiletin from a traditional herbal medicine, *Aurantii Fructus Immaturus*", Jpn. J. Pharmacol., vol. 66, pp. 139-147.

Telang et al., (1990), "Neoplastic transformation of mouse mammary epithelial cells by deregulated *myc* expression", Cell Regulation, vol. 1, pp. 863-872.

Tokuda et al., (1986). "Inhibitory effects of ursolic and oleanolic acid on skin tumor promotion by 12-O-tetradecanoylphorbol-13-acetate", Cancer Letters, vol. 33, pp. 279-285.

Verhoeven et al., (1996), "Epidemiological studies on brassica vegetables and cancer risk", Cancer Epidemiology, Biomarkers and Prevention, vol. 5, pp. 733-748.

Weisburger et al., (1998), "Effect of black tea on azoxymethane-induced colon cancer", Carcinogenesis, vol. 19, 1, pp. 229-232.

Yang et al., (1997), "Black tea constituents, theaflavins, inhibit 4-(methylnitrosamino)-1-(3-pyridyl)-1-butanone (NNK)-induced lung tumorigenesis in A/J mice". Carcinogenesis, vol. 18, 12, pp. 2361-2365.

"Colon cancer prevention and citrus flavonoid," *Nutrition Research Newsletter* 17(7-8) (1998).

"Fruit with a pun," *Natural Health* pp. 116-119,187(Jul.-Aug. 1998).

"Fruitful findings on cancer," *Tufts University Diet & Nutrition Letter* p. 6 (Aug. 1996).

Attaway, "Citrus juice flavonoids with anti-cancer properties," *Abstracts of Papers of the American Chemical Society,*, 204:P184-AGFD (1992) [abstract].

Boterberg et al., "Inhibition of the tamoxifen by the citrus favonoid tangeretin: an NK cell mediated effect?" *Acta Clinica Belgica* 54(2):109 (1999) [abstract].

Bracke et al., "Citrus flavonoid effect on tumor invasion and metastasis the citrus flavonoid tangeretin may inhibit the processes that shorten the life expectancy of tumor-bearing patients," *Food Technology, Institute of Food Technologists*, Chicago, US, 48(11):121-124 (1994).

Bracke et al., "Influence of tangeretin on tamoxifen's therapeutic benefit in mammary cancer," *J. National Cancer* Institute 91(4):354-359 (1999).

Bracke et al., "The citrus flavonoid tangeretin enhances cell-cell adhesion and inhibits invasion of human MCF-7/6 breast carcinoma cells," *Abstracts of Papers American Chemical Society* 208(1-2): pAGFD 81 [abstract] (1994).

Bracke et al., "The flavonoid tangeretin inhibits invasion of $MO_4$ mouse cells into embryonic chick heart *in vitro*," *Clin. Expl. Metastasis* 7(3):283-300 (1989).

Bracke et al., "Tangeretin affects human mammary cell interactions," *Abstracts of Papers American Chemical Society* 219 (1-2): pAGFD 184 (2000).

Breinholt et al., "Differential effects of dietary flavonoids on drug metabolizing and antioxidant enzymes in female rat," *Xenobiotica* 29(12):1227-1240 (1999).

Carroll et al., "Anticancer properties of flavonoids, with emphasis on citrus flavonoids," *Flavonoids in Health and Disease*, Rice-Evans CA, Parker L, eds., Marcel Dekker Inc, NY, Chapter 19, pp. 437-446 (1998).

Chaumontet et al., "Apigenin and tangeretin enhance gap junctional intercellular communication in rat liver epithelial cells," *Carcinogenesis* 15(10):2325-2330 (1994).

Chaumontet et al., "Flavonoids (apigenin, tangeretin) conteract tumor promoter-induced inhibition of intercellular communication of rat liver epithelial cells," *Cancer Letters* 114:207-210 (1997).

Chaumontet et al., "Lack of tumor-promoting effects of flavonoids: studies on rat liver preneoplastic Foci and on *in vivo* and *in vitro* gap junctional intercellular communication," *Nutr. Cancer* 26:251-263 (1996).

Chen et al., "Two new polymethoxylated flavones, a class of compounds with potential anticancer activity, isolated from cold pressed dancy tangerine peel oil solids," *J. Agric. Food Chem.* 45:364-368 (1997).

Craig, "Foods that help fight cancer," *Vibrant Life* 14(4):16 (1998).

Deschner et al., "Quercetin and rutin as inhibitors of azoxymethanol-induced colonic neoplasia," *Carcinogenesis* 12(7):1193-1196 (1991).

Gilbert, "Vital signs: remedies; surprise finding on tamoxifen and citrus," *New York Times* F7 Mar. 2, 1999 (1999).

Guthrie and Carroll, "Inhibition of human breast cancer cell growth and metastasis in nude mice by citrus juices and their constituent flavonoids," *Biological Oxidants and Antioxidants: Molecular Mechanisms and Health Effects*, edited by Lester Packer and Augustine S.H. Ong, Aocs Press, Champaign, Illinois, Chapter 35 pp. 310-316 (1998).

Guthrie and Carroll, "Inhibition of mammary cancer by citrus flavonoids," *Flavonoids in the Living System* edited by Mantey and Buslig, Plenum Press, New York, Chapter 16 227-236 (1998).

Guthrie and Kurowska, "Anticancer and cholesterol-lowering activities of citrus flavonoids," *Handbook of Nutraceuticals and Functional Foods*, Edited by Robert E.C. Wildman, CRC Press, Chapter 7 pp. 113-126 (2001).

Guthrie et al., "Combined effects of palm oil tocotrienols, flavonoids and tamoxifen on the proliferation of estrogen receptor-positive MCF-7 human breast cancer cells," *Proceedings of the American Association for Cancer Research* 37:280 (1996).

Guthrie et al., "In vitro studies on anti-cancer and cholesterol-lowering activities of citrus flavonoids and limonoids," *FASEB Journal, Fed. of American Soc. For Experimental Biology*, BVethesda, MD, US 14(15):A563 (Mar. 2000).

Hirano et al., "Citrus flavone tangeretin inhibits leukaemic HL-60 cell growth partially through induction of apoptosis with less cytotoxicity on normal lymphocytes," *British Journal of Cancer* 72:1380-1388 (1995).

Hirano et al., "Natural flavonoids and lignans are potent cytostatic agents against human leukemic HL-60 cells," *Life Sciences* 55(13):1061-1069 (1994).

Huachong, "Origin confirmation of a new natural product from *Oldenlandia diffusa*," *Journal of Chinese Medicinal Materials* 21(6):301-302 (1998) [Chinese w/English abstract].

Iwase et al., "Inhibitory effect of flavonoids from *Citrus* plants on Epstein-Barr virus activation and two-stage carcinogenesis of skin tumors," *Cancer Letters* 154:101-105 (2000).

Kandaswami et al., "Antiproliferative effects of citrus flavonoids on a human squamous cell carcinoma in vitro," *Cancer Letters* 56:147-152 (1991).

Kandaswami et al., "Differential inhibition of proliferation of human squamous cell carcinoma, gliosarcoma and embryonic fibroblast-like lung cells in culture by plant flavonoids," *Anti-Cancer Drugs* 3:525-530 (1992).

Kawaii et al., "Antiproliferative activity of flavonoids on several cancer cell lines," *Biosci. Biotechnol. Biochem.* 63(5):896-899 (1999).

Kawaii et al., "Effect of citrus flavonoids on HL-60 cell differentiation," *Anticancer Research* 19:1261-1269 (1999).

Kawaii et al., "Quantitation of flavonoid constituents in *Citrus* fruits," *J. Agric. Food Chem.* 47:3565-3571(1999) [In Japanese, no English abstract available at time of filing].

Kinoshita et al., "Differentiation induction of murine leukemia cells by flavonoids," *J. Pharmacobio-Dyn.* 8:s-122 (1985).

Kinoshita et al., "Induction of differentiation in murine erythroleukemia cells by flavonoids," *Chem. Pharm. Bull.* 33(9):4109-4112 (1985).

Lake et al., "Inhibition of xenobiotic-induced genotoxicity in cultured precision-cut human and rat liver slices," *Mutation Research* 440:91-100 (1999).

Le Bon et al., "Inhibition of microsome-mediated binding of benzo[alpha]pyrene to DNA by flavonoids either *in vitro* or after dietary administration to rats," *Chem.-Biol. Interacations* 83:65-71 (1992).

Malterud, "Flavonoids from *Orthosiphon spicatus*," *Planta Medica* 55:569-570 (1989).

Manthey et al., "Biological properties of citrus flavonoids pertaining to cancer and inflammation," Current Medicinal Chemistry 8:135-153 (2001).

Manthey et al., "Methoxylated citrus flavones suppress cytokine expression by monocytes," Abstracts of Papers American Chemical Society 217(1-2):pMEDI 212 (1999) [abstract].

Manthey et al., "Polymethoxylated flavones derived from citrus suppress tumor necrosis factor-alpha expression by human monocytes," *J. Nat. Prod.* 62:441-444 (1999).

Middleton and Kandaswami, "Potential health-promoting properties of citrus flavonoids," *Food Technology* pp. 115-119 (Nov. 1994).

Murakami et al., "Inhibitory effect of citrus noiletin on phorbol ester-induced skin inflammation, oxidative stress, and tumor promotion in mice," Cancer Research 60:5059-5066 (2000).

Murakami et al., "Suppressive effects of citrus fruits on free radical generation and nobiletin, an anti-inflammatory polymethoxyflavonoid," *BioFactors* 12:187-192 (2000).

Rouseff and Nagy, "Health and nutritional benefits of citrus fruit components," *Food Technology* 125-126, 128-129,132 (Nov. 1994).

Siess et al., "Mechanisms involved in the chemoprention of flavonoids," *BioFactors* 12:193-199 (2000).

So et al., "Inhibition of human breast cnacer cell proliferation and delay of mammary tumorigenesis by flavonoids and citrus juices," *Nutrition and Cancer* 26(2):167-181 (1996).

Soma et al., "Regulation of gene expression during redifferentiation of promoyelocytic leukemia cells HL-60 by 12-*O*-tetradecanoylphorbol-l3-acetate," *J. Pharmacobio-Dyn.* 8:s-123 (1985).

Tsuchiya and Yamane, "Cotransport of Na+ and amino acids in *Escherichia coli*," *J. Pharmacobio-Dyn.* 8:s-124 (1985).

Vines, "Fruity formula could contain prostate cancer (Possible oral medication for containing prostate cancer)," *New Scientist* p. 18 (1995).

Peirce, A. The American Pharmaceutical Association Practical Guide to Natural Medicines, 1999, Stonesong Press, Inc., pp. 551-554.

Rooprai et al., "Influence of putative antiinvasive agents on matrix metalloproteinase secretion by human neoplastic glia *in vitro*," Annals New York Academy of Sciences 878:654-657 (1999).

Attaway J.A., (1994), "Citrus Juice Flavonoids with Anticarciongenic and Antitumor Properties", Food Phytochemicals for Cancer Prevention, ACS Symposia Series, #546, pp. 240-248.

Bradlow et al., (1991), "Effect of dietary indole-3-carbinol on estradiol metabolism and spontaneous mammary tumors in mice", Carcinogenesis, vol. 12, pp. 1571-1574.

Calomme et al., (1996), "Inhibition of bacterial mutagenesis by citrus flavonoids", Planta Medica, vol. 62, pp. 222-226.

Fujiki et al., (1996), "Japanese green tea as a cancer preventive in humans", Nutrition Reviews, vol. 54, pp. S67-S70.

Huang et al., (1994), "Inhibition of skin tumorigenesis by rosemary and its constituents carnosol and ursolic Acid", Cancer Research, vol. 54, pp. 701-708.

Ito et al., (1999), "The citrus flavonoid nobiletin suppresses the production and gene expression of matrix metalloproteinases-9/ gelatineaseB in rabbit sunovial cells", Ann N Y Acad. SCI, vol. 878, pp. 632-634.

Iwase et al., "Cancer chemopreventive activity of 3.5.6.7.8.3'4'-heptamethoxyflavone from the peel of citrus plants", Cancer Letters, vol. 163, pp. 7-9, Feb. 2001.

Javed et al., (1998), "Chemopreventive effects of black tea polyphenols in mouse skin model of Carciongenesis", Biomedical and Environmental Sciences, vol. 11, pp. 307-313.

Kawaii et al., (1999), "HL-60 differentiating activity and flavonoid content of the readily extractable fraction prepared from citrus juices". J. Agric. Food Chem., vol. 47, pp. 128-135.

Kohno et al., (2001), "Dietary administration of citrus nobiletin inhibits azoxymethane-induced colonic aberrant cryupt foci in rats", Life Sciences, vol. 69, pp. 901-913.

* cited by examiner

EXTRACTS OF ORANGE PEEL FOR PREVENTION AND TREATMENT OF CANCER

This application is the United States national stage of International Application No. PCT/US00/25733, filed Sep. 20, 2000, which was published under PCT Article 21 (2) in English as International Publication No. WO 01/21137, and which claims benefit of priority of U.S. Provisional Application No. 60/155,018, filed Sep. 21, 1999.

BACKGROUND OF THE INVENTION

Naturally occurring non-nutritive agents present in plants such as flavonoids, phenolic compounds, glucosinulates, terpenes and many others are believed to have disease preventive properties. Diets containing some of these substances have been shown to be protective against diseases such as colon and breast cancer in animals (Kuo, S. M. 1997. Clin. Rev. Oncogenesis 8:47–69; Verhoeven et al. 1996. Cancer Epid. Biomark. Prev. 5:733–748; Bradlow et al. 1991. Carcinogenesis 12:1571–1574; Lamartiniere et al. 1995. Proc. Soc. Exp. Biol. Med. 208:120–123). The clinical relevance of such natural phytochemicals is dependent on extrapolation from epidemiological data and from experiments in animal models of diseases of interest.

Purified flavenoid compounds isolated from citrus juice have been tested individually for their effects on carcinogenesis, tumor cell growth and invasion of tumor cells into normal cells (Attaway, J. A. 1994. In: *Food Phytochemicals for Cancer Prevention, ACS Symposia Series* #546, Huang et al. Eds., pp. 240–248) In particular the polymethyoxylated flavenoids, tangeretin and nobeletin, were shown to have anti-carcinogenic activity.

Extracts of bitter-orange peel are used as an herbal drug (Bisset, N. G. 1994. *Herbal Drugs and Phytopharmaceuticals*, CRC Press: Boca Raton). Conditions treated include loss of appetite and dyspeptic complaints. The main components of the extract include limonene and flavonoids such as neohesperidin and naringin.

Several patents disclose the use of various phytochemicals in combination with orange peel extract or dried orange peel. CN 1200277 describes use of a composition composed of 16 plant components, one of which is dried orange peel, for treatment of psychosis and nervous system disease. CN 1116945 describes the use of orange peel along with several other natural products in a capsule form to sooth the liver, nourish the stomach, remove stasis, stop pain and cure various gastric diseases. CN 1111134 discloses an oral liquid containing orange peel, among other things, for treatment of neurasthenia, chronic bronchitis, asthma, coronary heart disease, high blood lipid levels, hepatitis, cytopenia, senility and immune dysfunction. CN 1106673 is a patent for a disease-preventing nutrient tea that is produced from a variety of products, including soaked, crushed orange peel. CN 1077124 describes a Chinese herb preparation for treatment of iron-deficiency anemia that is composed of a number of ingredients, including dried orange peel. Finally, a Japanese patent (JP 57156761) discloses a heat-generating pad for orthopedic diseases that contains extracts and powders of many plants, including orange peel.

It has now been found that an extract of orange peel has biological activity as a treatment and preventative agent for cancer.

SUMMARY OF THE INVENTION

An object of the present invention is an extract of orange peel which comprises 4',5,6,7,8-pentamethoxyflavone and 3',4',5,6,7,8-hexamethoxyflavone. The composition may further comprise other polymethoxylated flavones.

Another object of the present invention is a composition which comprises an extract of orange peel and rosemary extract, a Mexican Bamboo extract, a Huzhang extract, resveratrol, a black tea extract, and/or a hydroxylated or methoxylated resveratrol analog.

Another object of the present invention is to provide a method for inhibiting tumor cell growth in an animal comprising administering to an animal an orange peel extract which is administered alone or in combination with rosemary extract, a Mexican Bamboo extract, a Huzhang extract, resveratrol, a black tea extract, and/or a hydroxylated or methoxylated resveratrol analog.

Another object of the present invention is to provide a method for preventing or treating cancer in an animal which comprises administering to an animal an effective amount of an orange peel extract which is administered alone or in combination with rosemary extract, a Mexican Bamboo extract, a Huzhang extract, resveratrol, a black tea extract, and/or a hydroxylated or methoxylated resveratrol analog.

DETAILED DESCRIPTION OF THE INVENTION

Unlike many phytochemicals, orange peel extract is lipid soluble, a property which is desirable in many drug products because passage across biological membranes, and ultimately bioavailability, is enhanced. Orange peel and its extracts have been used in a variety of herbal drug products in combination with many different plant components and extracts. However, none of the previous research on orange peel or its extracts has examined or demonstrated activity against tumor cell growth or cancer. It has now been shown that orange peel extract inhibits tumor growth in vivo.

Orange peel extract is a mixture of highly bioactive and organic soluble, methylated flavonoids. An extract was obtained from cold-pressed peel oil solids, a waste product from the orange juice industry. The peel oil solids were dissolved in warm ethanol and, after several repeated washes, became a standardized product, with a reproducible amount of flavonoids. The extract comprises a mixture of various analogs and homologs of methylated flavonoids.

Experiments were performed to isolate and identify components in the orange peel extract. Methylated flavonoids from the orange peel extract were analyzed by either reverse-phase or normal-phase high performance liquid chromatography (HPLC). During normal phase HPLC the conditions included use of a silica gel HPLC column (Mac-Mod Analytical Co., Chadds Ford, Pa.) of dimensions 4.6 mm i.d.×25 cm length and a solvent gradient that started at 90% hexane and went to 90% chloroform in 20 minutes with a final hold at 90% chloroform for an additional 20 minutes. Separated components or peaks were then identified using HPLC coupled with mass spectrometry (HPLC-MS). Atmospheric pressure chemical ionization mass spectrometry was used for molecular weight determinations. HPLC-MS techniques such as particle beam (EI) introduction was used to produce standard fragmentation patterns of the methylated flavonoids. Standards for many of the compounds were obtained from the Florida Department of Citrus. Using these techniques the following components were identified: 5,6,7,3',4'-pentamethoxyflavone (also known as sinensetin), 5,6, 7,8,3',4'-hexamethoxyflavone (also known as nobeletin), 5,6,7,8,4'-pentamethoxyflavone (also known as tangeretin), 5-hydroxy-6,7,8,3',4'-pentamethoxyflavone (also known as auranetin), 5-hydroxy-7,8,31,4'-methoxyflavone, 5,7-hydroxy-6,8,3',4'-methoxyflavone, 5,7,8,3',4'-pentamethoxyflavone, 5,7,8,4'-methoxyflavone, 3,5,6,7,8,3',4'-methoxyflavone, 5-hydroxy-3,6,7,8,3',4'-methoxyflavone, 5-hydroxy-6,7,8,4'-methoxyflavone, 5,6,7,4'-methoxyflavone, 7-hydroxy-3,5,6,8,3',4'-methoxyflavone, and 7-hydroxy-3,5,6,3',4'-methoxyflavone.

The in vivo tumor inhibitory effects of the complete (including all 14 identified compounds) orange peel extract was tested in an orthotransplant model (Telang, N. T. et al. 1990. *Cell Regulat.* 1:863–872). Mice were transplanted with oncogene-expressing, preneoplastic breast epithelial cells. Mice were then divided into groups with the control group fed AIN-76A diet alone. Another group of mice was fed AIN-76A diet supplemented with 5000 ppm orange peel extract. After 12 weeks of continuous feeding, all mice in the control group exhibited palpable tumor formation at the transplant sites (1000 tumor incidence). In contrast, the group fed diet supplemented with the orange peel extract had a 0% tumor incidence (0/5 mice). Weight gains in the groups were comparable indicating that the orange peel extract had little to no systemic toxicity.

The orange peel extract was then tested in an in vivo model for colon cancer. Female CF-1 mice were injected with azoxymethane (AOM) once a week for four weeks at increasing doses (5, 10, 10 and 10 mg/kg). Orange peel extract was administered in the diet (0.2%) starting two weeks before the first AOM injection, during and continuing until the end of the experiment at 24 weeks. At week 24, the mice were given one last dose of AOM (10 mg/kg). The mice were then sacrificed and their colons removed (from anus to caecum). The colons were opened longitudinally, rinsed with normal saline, and stapled to a plastic sheet. The colon samples were placed in a 10% neutral buffered formalin solution for 24 hours. The entire colon was stained with 0.2% methylene blue dissolved in phosphate buffered saline for 20 minutes. The whole mount of colon samples were then examined using light microscopy for the presence of aberrant crypt (AC) or aberrant crypt foci (ACF). Both ACF and AC are biomarkers for colon cancer. Cancer prevention diets have been shown to reduce formation of ACF and AC. Mice fed nordihydroxyguaiaretic acid (NDGA) in the diet (0.2%) were used as controls. The results are shown below in Table 1.

TABLE 1

Effect of Feeding Orange Peel Extract on AOM-Induced Formation of Aberrant Crypt Foci (ACF) in Mice

| Lesion | Negative Control | Positive Control | 0.2% NDGA | 0.2% Orange Peel |
|---|---|---|---|---|
| ACF/colon | 0 | 5.2 ± 1.2 | 2.7 ± 0.9 | 2.7 ± 0.8 |
| AC/colon | 0 | 37 ± 5.9 | 9.4 ± 2.2 | 12.6 ± 2.8 |
| AC/ACF | 0 | 7.1 | 3.5 | 4.7 |
| ACF: 1 AC/colon | 0 | 15.0 ± 2.5 | 6.8 ± 1.5 | 6.4 ± 1.4 |
| ACF: 2 AC/colon | 0 | 5.5 ± 1.2 | 1.0 ± 0.3 | 2.0 ± 0.3 |
| ACF: 3 AC/colon | 0 | 1.0 ± 0.4 | 0.2 ± 0.2 | 0.2 ± 0.2 |
| ACF: 4 AC/colon | 0 | 1.0 ± 0.4 | 0 | 0.2 ± 0.2 |
| ACF: 5 AC/colon | 0 | 0.2 ± 0.2 | 0 | 0 |
| ACF: 6 AC/colon | 0 | 0.3 ± 0.3 | 0 | 0.2 ± 0.23 |
| ACF: 7 AC/colon | 0 | 0.2 ± 0.2 | 0 | 0 |

There was a 48% and 48% inhibition of the number of ACF per colon with NDGA and orange peel extract treatment, respectively. In addition, the ratio of AC/ACF was inhibited by 51% and 34%, with NDGA and orange peel extract treatment, respectively. These data demonstrate the efficacy of the orange peel extract in this animal model of colon cancer.

In a similar experiment in the mouse colon cancer model, CF-1 mice were injected with AOM (5, 10, 10 and 10 mg/kg) starting at 6 weeks of age, once each week and then once at 37 weeks after the first dose of AOM. Throughout the treatment period, mice received either an AIN 76A diet or test compound in AIN 76A diet at 2 weeks before the first dose of AOM and continuing until the end of the experiment. The test compounds were NDGA (0.2%) and orange peel extract (0.2%). Colon samples were again obtained at sacrifice, stored in 10% formalin phosphate buffer, and then colon tumor number was determined. The results are shown in Table 2.

TABLE 2

Effect of Dietary Orange Peel Extract Treatment on AOM-Induced Colon Tumorigenesis in Mice

| Treatment | Number of Animals | Body Weight (g) | Colon Tumors Per Mouse | Percent Incidence (%) |
|---|---|---|---|---|
| no AOM (negative control) | 15 | 51.3 ± 1.9 | 0 | 0 |
| AOM | 27 | 46.7 ± 1.9 | 0.52 ± 0.12 | 44 |
| 0.2% NDGA + AOM | 11 | 45.8 ± 2.1 | 0.27 ± 0.14 | 27 |
| 0.2% Orange Peel + AOM | 17 | 46.7 ± 2.2 | 0.29 ± 0.11 | 29 |

The data show that treatment with orange peel extract inhibited tumor development in AOM-treated mice to the same extent as the control comparison compound, NDGA, supporting the efficacy of orange peel extract as an antitumorigenic agent.

In addition to testing for the activity of the complete orange peel extract, two of the identified extract components, tangeretin and nobeletin, were tested for their combined activity in a cell proliferation assay. The growth of W138 (normal) and W138VA (transformed) cells was tested in the presence of a mixture of tangeretin and nobeletin. The dye crystal violet was used for measuring growth of the cells. Cells were treated with either tangeretin alone (0, 1, 5, 10, 20 or 50 μg/ml), nobeletin alone (0, 1, 5, 10, 20 or 50 μg/ml) or a mixture of the two compounds at a total concentration of the two flavenoids of 0, 1, 5, 10, 20 or 50 μg/ml. When used alone, tangeretin and nobeletin produced only marginal effects to inhibit cell growth in transformed cells, even at the highest dose tested, and had no effect on normal cell growth. In contrast, when administered as a mixture, tangeretin and nobeletin showed synergistic activity, with growth inhibition produced in transformed cells, in a dose dependent manner. There was no appreciable effect of the mixture on normal cell growth. These data confirm the results of the experiment in whole animals where orange peel extract, containing tangeretin and noveletin, had anti-tumorigenic activity. Further, when an extract containing 30% of the methylated flavenoids, including tangeretin and nobeletin was tested in this same assay there were significant inhibitory effects of cell proliferation at doses of 20 and 50 μg/ml. The range of doses of the extract tested was 0, 1, 5, 10, 20 and 50 μg/ml. These data provide evidence for a synergistic effect of the polymethylated flavonoids in arresting and inhibiting the growth of tumor cells.

Experiments were also performed in a preclinical cell culture model for human ductal breast carcinoma in situ (DCIS). The human breast-derived preneoplastic cell line 184-B5/HER expressed HER-2/neu, p53 and EGFR but not ER, therefore resembling the clinical DCIS. Initial dose-response experiments compared the growth inhibitory effect of orange peel extract on the parental 184-B5 cells and the HER-2/neu oncogene-expressing 184-B5/HER cells. Relative to parental cells, orange peel extract was at least two times more effective as a growth inhibitor for 184-B5/HER cells. Orange peel extract at the maximum cytostatic dose of 100 ppm accumulated the cells in the G0/G1 phase and inhibited the S+G2/M phase of the cell cycle, leading to down-regulation of cell cycle progression. This alteration in the cell cycle progression resulted in a 5-fold increase in the G0/G1: S+G2/M ratio. Treatment of 184-B5/HER cells with 100 ppm orange peel extract resulted in a 47.5% decrease in immunoreactivity to phosphotyrosine (marker for tyrosine kinase activity) and a 157.7% increase in immunoreactivity to the cyclin dependent kinase inhibitor p16$^{INK4}$. In addition, there was a selective induction of apoptosis in 184-B5/HER cells but not in parental 184-B5 cells. Treatment of 184-B5/HER cells with 100 ppm orange peel extract induced a 7.6-fold increase in sub G0/G1 (apoptotic) population. Consistent with the induction of apoptosis, immunoreactivity to anti-apoptotic Bcl-2 was decreased by 33%.

Based upon the experiments described herein, it is believed that compositions comprising orange peel extract or a combination of components of the orange peel extract including but not limited to tangeretin and nobeletin, may be included in foods and dietary supplements or "nutraceuticals" for prevention or treatment of cancer. One of skill can use the results of experiments in cells and animals described herein to determine effective amounts to be administered to other animals, including humans. By "effective amount" it is meant a concentration that inhibits tumor growth either in vitro in cells or in vivo in animals. For example, human test doses can be extrapolated from effective doses in cell studies, such as IC$_{50}$ values, or from effective doses in vivo by extrapolating on a body weight or surface area basis. Such extrapolations are routine in the art. Compositions comprising orange peel extracts can be formulated for administration as a food supplement using one or more fillers. Alternatively, compositions comprising these extracts can be administered as conventional pharmaceuticals using one or more physiologically acceptable carriers or excipients. Nutraceutical compositions can be formulated for administration by any route including, but not limited to, inhalation or insufflation (through mouth or nose), oral, buccal, parenteral, vaginal, or rectal administration. In one embodiment, oral administration, the compositions are added directly to foods and ingested as part of a normal meal. Various methods are known to those skilled in the art for addition or incorporation of nutraceuticals into foods.

Compositions for use in the present invention can also be administered in the form or tablets or capsules prepared by conventional means with pharmaceutically acceptable excipients such as binding agents, fillers, lubricants, disintegrants, or wetting agents. Examples of specific compounds for use in formulating tablets and capsules are described in detail in the U.S. Pharmacopeia. Tablets comprising the extract can also be coated by methods well known in the art. Liquid preparations for oral administration can also be used. Liquid preparations can be in the form of solutions, syrups or suspensions, or a dry product for reconstitution with water or another suitable vehicle before use. Such liquid preparations can be prepared by conventional means with pharmaceutically acceptable additives such as suspending agents, emulsifying agents, non-aqueous vehicles, and preservatives. Again, specific additives are well known to those of skill and are listed in places such as the U.S. Pharmacopeia. In one embodiment, the oral preparation is formulated to provide controlled time release of the active nutraceutical components. For buccal administration the extract can be formulated as a tablet or lozenge.

For administration by inhalation, compositions for use in the present invention can be delivered in the form of an aerosol spray in a pressurized package or as a nebulizer, with use of suitable propellants. In the case of a pressurized aerosol, the dosage unit can be determined by providing a valve to deliver a metered dose.

Parenterally administered compositions are formulated to allow for injection, either as a bolus or as a continuous infusion. Formulations for injection can be prepared in unit dosage forms, such as ampules, or in multi-dose units, with added preservatives. The compositions for injection can be in the form of suspensions, solutions, or emulsions, in either oily or aqueous vehicles. They may also contain formulatory agents such as suspending agents, stabilizing agents, and/or dispersing agents. The active ingredient may also be presented in powder form for reconstitution with a suitable vehicle before use. Specific examples of formulating agents for parenteral injection are found in the U.S. Pharmacopeia.

For rectal administration or vaginal administration, compositions for use in of the present invention can be formulated as suppositories, creams, gels, or retention enemas.

For dietary supplements, the extract can be added in concentrations up to 5% by weight and mixed according to methods routine in the art. Dietary supplements for animals can be prepared in a variety of forms including, but not limited to, liquid, powder, or solid pill forms. In the present invention, the orange peel extract can administered either alone or in combination with other phytochemicals known to affect tumor cell growth, where combining compounds or extracts would lead to synergistic effects. Examples of other phytochemicals which can be used in combination with orange peel extract include, but are not limited to, resveratrol and its hydroxylated and methoxylated analogs, rosemary extract, black tea extracts, Mexican Bamboo, and Huzhang extracts.

Many plants, such as Mexican Bamboo and Huzhang, contain high amounts of an active component known as resveratrol. Resveratrol is a well known, biologically active phytochemical. Resveratrol and its hydroxylated and methoxylated analogs have been shown to have activity both in vitro and in vivo to affect cell proliferation and tumor cell growth. Resveratrol and several of its analogs (3,5-dihydroxystilbene: R-1; 3,3',4,5'-tetrahydroxystilbene: R-2;3,4,4',5-tetrahydroxystilbene: R-3; 3,3',5,5'-tetrahydroxystilbene (R-4), 3,3',4,5,5'-pentahydroxystilbene: R-5; 3,5-dimethoxystilbene: MR-1;3, 4',5-trimethoxystilbene: MR-0; 3,3',4,5'-tetramethoxystilbene: MR-2; 3,4,4',5-tetramethoxystilbene: MR-3; 3,3',5'5'-tetramethoxystilbene: MR-4; and 3,3',4,5,5'-pentamethoxystilbene: MR-5) were evaluated in cell culture studies using standard methodologies.

W138 human diploid fibroblasts and cancerous SV40-transformed W138 cells (W138VA) were used in a cell proliferation assay. Growth rate and viability of these cells was determined following addition of resveratrol or one of its analogs. Doses tested ranged from 50 ng to 300 μg per ml or 1 μM to 100 μM concentrations in culture media. Resveratrol inhibited cell growth at concentrations less than 10 μM. The resveratrol analogs R3 and MR-0 also inhibited cell growth. At a concentration of 1 μM, MR-3 completely blocked proliferation of W138VA cells, although it had no effect on growth of W138 cells. MR-4 inhibited growth of W138 cells but not W138VA cells at doses of 100 μM. MR-1 was not active as an inhibitor of cell growth even at doses as high as 100 μM.

Treatment of W138 and W138VA cells with resveratrol and its analogs also led to morphological changes in the cells. Treatment of W138 cells with resveratrol and its analogs R-1 and R-3 led to elongation of normal W138 cells. Methoxy analogs such as MR-0 and MR-3 caused the flattening of W138 cells. This flattening was accompanied by an increase in neutral β-galactosidase activity as indicated by an increase in staining. An increase in activity of β-galactosidase is characteristic of senescent cells, indicating that these analogs modulate the life-span of normal cells.

Resveratrol and its analogs were also tested in preneoplastic 184-B5/HER human mammary epithelial cells. Results showed that there was a dose-dependent inhibition of growth in response to treatment with resveratrol as well as the methoxy derivatives MR-0, MR-2 and MR-3. The concentration that inhibited growth by 50% ($IC_{50}$) for the tested compounds were: resveratrol, 10.5 μM; MR-0, 10.5 μM; MR-2 120 μM; MR-3, 1.0 μM. A cell cycle analysis revealed that treatment with MR-0, MR-2 and MR-3 resulted in progressive arrest of cells in the G2/M phase relative to solvent-treated control cultures and that MR-3 was the most effective compound.

The in vivo tumor inhibitory effects of MR-3 were tested in an orthotransplant model. Mice were transplanted with oncogene-expressing, preneoplastic breast epithelial cells. Mice were then divided into groups with the control group fed AIN-76A diet alone. Another group of mice was fed AIN-76A diet supplemented with MR-3 (400 ppm). After 12 weeks of continuous feeding, all mice in the control group exhibited palpable tumor formation at the transplant sites (100% tumor incidence). In contrast, the group fed diet supplemented with the analog MR-3 had a 20% tumor incidence, with only one mouse of the five tested exhibiting tumor growth. Weight gains in the groups were comparable indicating that the analog had little toxicity.

This series of studies, both in vitro and in vivo, indicated that resveratrol as well as analogs of resveratrol have biological activity related to preventing progression of cancer in cells.

Extracts of rosemary have also been shown to have anti-tumor activity and chemopreventive properties (Huang et al. 1994. Cancer Res.54:701–708; Tokuda et al. 1986. Cancer Lett. 33:279–285; Singletary et al. 1996. Cancer Lett. 104:43–48; Singletary, K. W. and J. M. Nelshoppen. 1991. Cancer Lett. 60:169–175). For example, a diet containing 1% of rosemary extract significantly inhibited the initiation of mammary tumorigenesis in rats (Singletary, K. W. and J. M. Nelshoppen. 1991. Cancer Lett. 60:169–175). Palpable tumor incidence in rats fed the rosemary extract was 47% less than that of rats fed a control diet. Therefore, rosemary extracts were cancer preventive.

Black tea and its extracts have also been well-studied as potential pharmacological agents. Epidemiological studies have suggested that tea consumption has a protective effect against certain forms of human cancer (Stoner, G. D. and H. Mukhtar. 1995. J. Cell Biochem. Suppl. 22:169–180; Fujiki et al. 1996. Nutr. Rev. 54:S67-S70). In addition, extracts of black tea in particular have been shown to be potent inhibitors of tumorigenesis in several animal model systems (Javed et al. Biomed. Environ. Sci. 11:307–313; Yang et al. 1997. Carcinogenesis 18:2361–2365; Weisberger et al. 1998. Carcinogenesis 19:229–232; Rogers et al. 1998. Carcinogenesis 19:1269–1273). Therefore, black tea extracts are known to be tumor preventive agents.

Accordingly, it is believed that a combination diet of dietary supplement comprising orange peel extract and at least one other phytochemical will also be useful to treat or prevent cancer in animals, including humans. Orange peel extract may be used in combination with rosemary extract, resveratrol and its analogs, Mexican Bamboo or Huzhang extracts, and black tea extracts. Doses of each extract used in the combination product are selected based on known activity of the extract in animals or cells.

What is claimed is:

1. A method for treating colon cancer in a human, comprising administering to said human in need of such treatment an effective amount of a composition comprising the following flavone components: 5,6,7,3',4'-pentamethoxyflavone; 5,6,7,8,3',4'-hexamethoxyflavone; 5,6,7,8,4'-pentamethoxyflavone; 5-hydroxy-6,7,8,3',4'-pentamethoxyflavone; 5-hydroxy-7,8,3',4'-tetramethoxyflavone; 5,7-dihydroxy-6,8,3',4'-tetramethoxyflavone; 5,7,8,3',4'-pentamethoxyflavone; 5,7,8,4'-tetramethoxyflavone; 3,5,6,7,8,3',4'-heptamethoxyflavone; 5-hydroxy-3,6,7,8,3',4'-hexamethoxyflavone; 5-hydroxy-6,7,8,4'-tetramethoxyflavone; 5,6,7,4'-tetra methoxyflavone; 7-hydroxy-3,5,6,8,3',4'-hexamethoxyflavone; and 7-hydroxy-3,5,6,3',4'-pentamethoxyflavone.

2. The method of claim 1, wherein the composition is a dietary supplement.

3. The method of claim 2, wherein the amount administered corresponds to an approximately 5000 ppm supplement of the human's diet.

4. The method of claim 2, wherein the amount administered corresponds to approximately 0.2% of the human's diet.

5. The method of claim 1, wherein the composition is a food supplement.

6. The method of claim 5, wherein the amount administered corresponds to an approximately 5000 ppm supplement of the human's diet.

7. The method of claim 5, wherein the amount administered corresponds to approximately 0.2% of the human's diet.

8. The method of claim 1, wherein the composition is administered in the form of a capsule.

9. The method of claim 1, wherein the composition is administered in the form of a tablet.

10. The method of claim 1, wherein the composition is administered in the form of a pill.

11. The method of claim 1, wherein the composition further comprises resveratrol, hydroxylated analogs of resveratrol, or methoxylated analogs of resveratrol.

12. The method of claim 1, wherein the composition further comprises a rosemary extract, a black tea extract, a Mexican Bamboo extract, or a Huzhang extract.

* * * * *